United States Patent [19]

Borgardt et al.

[11] 4,182,921
[45] Jan. 8, 1980

[54] METHOD OF PURIFYING ALKYLPHENOL

[76] Inventors: Valentina J. Borgardt, ulitsa Imaya Masyri, 1, kv. 193, Bashkirskaya ASSR Sterlitamak; Jury I. Volodin, ulitsa Kalinina, 3, kv. 59, Kuibyshevskaya oblast Novokuibyshevsk; Zoya S. Shalimova, ulitsa Druzhby, 19, kv. 56, Bashkirskaya ASSR Sterlitamak; Boris T. Pantukh, ulitsa khudaiberdina 162, kv. 89, Bashkirskaya ASSR Sterlitamak; Sofya A. Egoricheva, ulitsa Nagumanova 56a, kv. 23, Bashkirskaya ASSR Sterlitamak; Grigory I. Rutman, Revoljutsionnaya ulitsa 7, kv. 6, Bashkirskaya ASSR Sterlitamak; Jury I. Michurov, prospekt Lenina, 13, kv. 4, Bashkirskaya ASSR Sterlitamak, all of U.S.S.R.

[21] Appl. No.: 796,302

[22] Filed: May 12, 1977

[51] Int. Cl.² .............................................. C07C 37/24
[52] U.S. Cl. .................................................... 568/750
[58] Field of Search ....................... 260/624 A, 627 R; 568/750

[56] References Cited
U.S. PATENT DOCUMENTS

| 2,493,781 | 1/1950 | Schneider et al. | 260/624 A |
| 2,536,040 | 1/1951 | Davidson | 260/624 A |

FOREIGN PATENT DOCUMENTS 697476  9/1953  United Kingdom ................ 260/624 A Primary Examiner—Werren B. Lone
Attorney, Agent, or Firm—Lackenbach, Lilling & Siegel

[57] ABSTRACT

A method of purifying alkylphenyl from impurities contained therein resides in continuous crystallization of alkylphenol and continuous washing of the resulting crystals with a solvent.

Washing of the crystals is performed in a layer formed by said crystals, the layer moving downward continuously, with a solvent moving upward.

The invention makes it possible to purify alkylphenols effectively and produce them with a high degree of purity with minimum losses of the product, as well as to reduce consumption of the solvent.

8 Claims, No Drawings

METHOD OF PURIFYING ALKYLPHENOL

The present invention relates to the production of phenol stabilizers, and more particularly to a method of purifying alkylphenols.

4-Methyl-2,6-di-tert.butylphenol is a representative of phenol stabilizers; it is a light-colored stabilizer which does not color the material being protected and is non-toxic.

4-Methyl-2,6-di-tert.butylphenol is used as a stabilizer for synthetic rubbers, polyethylene, chemical fibres as well as an antioxidative additive to oils, fuels, and other petroleum products.

4-Methyl-2,6-di-tert.butylphenol also finds application in the food industry for stabilizing solid animal oils, and in medicine.

Another representative of phenol stabilizers is bis-(5-methyl-3-tert. butyl-2-hydroxyphenol)-methane.

The known methods of purifying alkylphenols include crystallization of alkylphenols from a suitable solvent and washing of the resulting crystals with this solvent.

Known in the art is a method of purifying alkylphenols, for example, 4-methyl-2,6-di-tert.butylphenol, by crystallization from glycols.

This method is disadvantageous in that crystallization proceeds slowly and the required purity cannot be attained.

Likewise known in the art is a method of purifying alkylphenols, for example, 4-methyl-2,6-di-tert.butylphenol, by crystallizing it from a dilute isopropyl alcohol and washing the resultant crystals with said solvent. As a result, a yellow product is obtained with melting point of 64°–67° C.

The disadvantage of the method is that even repeated crystallization does not ensure the required purity of the product; in addition, a considerable amount of a solvent is needed for crystallization.

Crystallization of alkylphenols, in particular 4-methyl-2,6-di-tert-butylphenol, from an acetone: water mixture gives a pure product with a melting point of 69.5°–71.0° C.

The disadvantage of this method is that a considerable amount of the solvent is required for washing, and losses of the final product occur.

Crystallization of 4-methyl-2,6-di-tert.butylphenol from methyl alcohol gives a pure product with a melting point of 69.5°–70.0° C.

The method is disadvantageous in that crystallization is accompanied by losses of the final product as high as up to 15% by weight.

All the known methods of purifying alkylphenols are periodic.

It is an object of the invention to provide a continuous method of purifying alkylphenols from impurities, which will improve the quality of the product and reduce its losses.

Said object is accomplished in a method of purifying alkylphenols from impurities by crystallization and washing of the crystals with a solvent inert towards alkylphenol. The method, according to the invention, resides in the continuous crystallization of alkylphenols at a feed rate of alkylphenol solution from 0.12 to 0.31 $hr^{-1}$ and washing the resulting crystals in a layer formed by said crystals moving downward at a rate of from 0.1 to 1.0 $hr^{-1}$ with a solvent moving upward at a rate of from 0.09 to 0.35 $hr^{-1}$.

As a solvent use can be made of ethyl alcohol, methyl alcohol, isopropyl alcohol, acetone, gasoline, and any other suitable solvent which dissolves alkylphenol and impurities contained therein and is inert towards alkylphenol.

The present invention makes it possible to run the process continuously and to obtain alkylphenols with a high degree of purity. The content of the product is from 99.99 to 100 wt.%; the yield is high due to minimum losses of the product. The solvent consumption is reduced considerably. Alkylphenol, in particular, 4-methyl-2,6-di-tert.butylphenol, purified by using the herein-proposed method, meets all the requirements: its melting point is 69.5°–70° C., its color is white and the content of impurities therein is up to 0.01 wt.%.

The method is accomplished in a simple way. Crystallization is conducted in a continuous-action crystallizer fitted with a washing element in the form of a vertical tube. The initial alkylphenol containing impurities is fed continuously as a solution in ethyl or methyl alcohol into the crystallizer. The solvent is chosen depending on the nature of alkylphenol to be purified. The rate of feed of alkylphenol solution delivered for crystallization is 0.12 to 0.31 $hr^{-1}$. Crystallization is conducted under continuous stirring at a temperature from +15 to +20° C. The crystals formed in the crystallizer go continuously into the washing element and form a layer over the whole volume thereof. The layer of the crystals moves continuously downward at a rate of from 0.1 to 1.0 $hr^{-1}$. The solvent moves in the washing element upward at a rate of from 0.09 to 0.35 $hr^{-1}$. Thus, washing is performed in a layer of crystals which moves in a vertical direction.

The solvent dissolves impurities present on the surface of the crystals and, after having passed through the washing element in the upward direction, goes into the crystallizer where excess of the solvent is removed and can be recycled to the process. Washing and crystallization of alkylphenol are conducted in the same solvent. The washed crystals of the product go continuously into a sampler and then to drying.

The rate of feeding alkylphenol solution to crystallization, as stated above, ranges from 0.12 to 0.31 $hr^{-1}$. Although the crystallization process can be conducted at a lower rate of alkylphenol is it undesirable, since then the time of crystallization increases and the process is disturbed.

If alkylphenol is fed at a rate higher than specified above, crystallization becomes incomplete, which is also undesirable. Thus, the crystallization process is disturbed if the flow rate of alkylphenol is higher or lower than the above-cited limits.

The rates with which the layer of crystals and solvent move in the washing element must be within the above-specified range. When the rate of the layer of crystals is below 0.1 $hr^{-1}$, it is difficult to maintain the moving layer, and the process of washing is disturbed. When the rate is above 0.1 $hr^{-1}$, the risk of the mother liquor entering the washing element from the crystallizer becomes higher, which is undesirable, since the product being purified becomes contaminated.

If the solvent moves in the washing element at a rate below 0.09 $hr^{-1}$, the washing of the crystals is insufficient and the product being purified is contaminated.

If the solvent moves in the washing element at a rate above 0.35 $hr^{-1}$, there takes place longitudinal stirring of the crystals, causing turbulence, and entrainment by the solvent into the crystallizer. As a result the required layer of the crystals in the washing element is disturbed.

The ratio of the height of the moving layer of crystals to its diameter may be different, but is is desirable that it should be no less than 3.

As is seen from the detailed description, the invention can easily be realized in industry.

The present invention is of commercial value, since the solvent is consumed in smaller amounts than in the known methods, while the yield and purity of the product are higher.

For a better understanding of the present invention the following examples are given hereinbelow by way of illustration.

EXAMPLE 1

A crystallizer having a capacity of 1600 ml, fitted with a stirrer, a washing element and a sampler, is preliminarily filled with a mother liquor of 4-methyl-2,6-di-tert.butylphenol in ethyl alcohol saturated at +15° C.

Alkylphenol of the following composition is fed into the crystallizer at a rate of 0.12 hr$^{-1}$ under continuous stirring:

| | |
|---|---|
| 4-methyl-2,6-di-tert.butylphenol | 90 wt. % |
| monoalkylphenol | 3 wt. % |
| 2,6-di-tert.butylphenol | 3 wt. % |
| 2,4,6-tri-tert.butylphenol | 4 wt. % |

Alkylphenol is fed as a 50% solution in ethyl alcohol. Crystallization is run at +15° C. The crystals of 4-methyl-2,6-di-tert.butylphenol formed in the crystallizer move as a layer downwards through a vertical washing element, 30 mm in diameter and 300 mm in height, at a rate of 0.38 hr$^{-1}$. Ethyl alcohol moves in the washing element at a rate of 0.14 hr$^{-1}$ as a counterflow. The solvent, passing through the washing element upwards, washes the remaining impurities from the surface of the crystals, dissolves them and goes into the crystallizer, wherefrom the excess solvent is removed. The washed crystals of 4-methyl-2,6-di-tert.butylphenol from the washing element are delivered continuously into the sampler, and therefrom to drying. After 50 hours of operation, 4,000 g of 4-methyl-2,6-di-tert.butylphenol are obtained with a melting point of 69.5°–70° C. (69.0°–70.0° C. as reported in the literature). The composition of the crystalline product is:

| | |
|---|---|
| 4-methyl-2,6-di-tert-butylphenol | 99.99 wt. % |
| monoalkylphenol | 0.01 wt. % |

The obtained crystals are white.

EXAMPLE 2

Under the conditions described in Example 1 a 50% solution of alkylphenol in methyl alcohol of the following composition is fed into the crystallizer at a rate of 0.12 hr$^{-1}$:

| | |
|---|---|
| 4-methyl-2,6-di-tert-butylphenol | 94 wt. % |
| 2,6-di-tert.butylphenol | 3 wt. % |
| 2,4,6-tri-tert.butylphenol | 3 wt. % |

Methyl alcohol moves at a rate of 0.14 hr$^{-1}$ in counterflow to the crystals of 4-methyl-2,6-di-tert.butylphenol which move as a layer at a rate of 0.4 hr$^{-1}$ in the vertical washing element.

The crystals of 4-methyl-2,6-di-tert.butylphenol are taken off continuously through the sampler. After 50 hours of operation, 4,200 g of 4-methyl-2,6-di-tert.butylphenol are obtained with a melting point of 69.5°–70.0° C. The composition of the crystalline product is:

| | |
|---|---|
| 4-methyl-2,6-di-tert.butylphenol | 99.99 wt. % |
| 2,6-di-tert.butylphenol | 0.01 wt. % |

EXAMPLE 3

Under the conditions described in Example 1 a 50% solution of alkylphenol in ethyl alcohol of the following composition is fed at a rate of 0.31 hr$^{-1}$ into the crystallize:

| | |
|---|---|
| 4-methyl-2,6-di-tert.butylphenol | 94 wt. % |
| 2,6-di-tert.butylphenol | 3 wt. % |
| 2,4,6-tri-tert.butylphenol | 3 wt. % |

Ethyl alcohol moves at a rate of 0.35 hr$^{-1}$ in counterflow to the crystals of 4-methyl-2,6-di-tert.butylphenol, which move as a layer at a rate of 1.0 hr$^{-1}$ in the vertical washer. The crystals of 4-methyl-2,6-di-tert.butylphenol are taken off continuously through the sampler. After 50 hours of operation, 10,500 g of 4-methyl-2,6-di-tert.butylphenol are obtained with a melting point of 69.5°–70.0° C. The composition of the crystalline product is:

| | |
|---|---|
| 4-methyl-2,6-di-tert.butylphenol | 99.99 wt.% |
| 2,6-di-tert.butylphenol | 0.01 wt.% |

The crystals obtained are white.

EXAMPLE 4

Under the conditions described in Example 1 a 50% solution of alkylphenol in ethyl alcohol of the following composition is fed at a rate of 0.23 hr$^1$ into the crystallizer:

| | |
|---|---|
| 4-methyl-2,6-di-tert-butylphenol | 94 wt. % |
| 2,6-di-tert.butylphenol | 3 wt. % |
| 2,4,6-tri-tert.butylphenol | 3 wt. % |

Ethyl alcohol moves at a rate of 0.13 hr$^{-1}$ in counterflow to the crystals of 4-methyl-2,6-di-tert.butylphenol, which move as a layer at a rate of 0.13 hr$^{-1}$ in the vertical washing element. After 50 hours of operation, 7,900 g of 4-methyl-2,6-di-tert.butylphenol are obtained with a melting point of 69.5°–70.0° C.

| | |
|---|---|
| 4-methyl-2,6-di-tert.butylphenol | 99.99 wt. % |
| 2,6-di-tert.butylphenol | 0.01 wt. % |

The crystals obtained are white.

EXAMPLE 5

Under the conditions described in Example 1 a 30% solution of alkylphenol in gasoline of the following composition is fed at a rate of 0.12 hr$^{-1}$ into the crystallizer:

| | |
|---|---|
| bis-(5-methyl-3-tert.butyl-2-hydroxyphenyl)-methane | 98 wt. % |
| 2-tert.butyl-4-methylphenol | 1 wt. % |
| 2,6-di-tert.butyl-4-methylphenol | 1 wt. % |

Crystallization is conducted at +20° C. under stirring. The crystals of bis-(5-methyl-3-tert.butyl-2-hydroxyphenyl)methane formed in the crystallizer move as a layer at a rate of 0.24 hr$^{-1}$ in the vertical washing element where gasoline moves in counterflow at a rate of 0.09 hr$^{-1}$. The washed crystals of bis-(5-methyl-3-tert.butyl-2-hydroxyphenyl)-methane are delivered continuously to the sampler and thence to drying. After 20 hours of operation 1,000 g of bis-(5-methyl-3-tert.butyl-2-hydroxyphenyl)-methane are obtained with a melting point of 129.8–130.0° C. No impurities have been found in the product by chromatographic analysis.

EXAMPLE 6

Under the conditions described in Example 1 a 50% solution of alkylphenol in ethyl alcohol of the following composition is fed at a rate of 0.12 hr$^{-1}$ into the crystallizer:

| | |
|---|---|
| 2,6-di-tert.butylphenol | 98.7 wt. % |
| 2,4-di-tert.butylphenol | 0.55 wt. % |
| 2,4,6-tri-tert.butylphenol | 0.44 wt. % |
| ortho-tert.butylphenol | 0.31 wt. % |

Ethyl alcohol moves at a rate of 0.14 hr$^{-1}$ in counterflow to the crystals of 2,6-di-tert.butylphenol, which move as a layer at a rate of 0.4 hr$^{-1}$ in the vertical washing element. The crystals of 2,6-di-tert.butylphenol are taken off continuously through the sampler. After 50 hours of operation, 4,100 g of 2,6-di-tert.butylphenol are obained with a melting point of 35.5°–36° C. (the melting point as reported in the literature is 35.0°–36° C.) No impurities have been found in the product by chromatographic analysis.

EXAMPLE 7

Under the conditions described in Example 1 a 50% solution of alkylphenol in ethyl alcohol of the following composition is fed at a rate of 0.12 hr$^{-1}$ into the crystallizer:

| | |
|---|---|
| 2,4,6-tri-tert.butyl-phenol | 97.0 wt. % |
| 2,6-di-tert.butylphenol | 2.0 wt. % |
| 2,4-di-tert.butylphenol | 1.0 wt. % |

Ethyl alcohol moves at a rate of 0.14 hr$^{-1}$ in counterflow to the crystals of 2,4,6-tri-tert.butylphenol, which move as a layer at a rate of 0.38 hr$^{-1}$ in the vertical washing element. The crystals of 2,4,6-tri-tert.butylphenol are taken off continuously through the sampler. After 50 hours of operation, 4,300 g of 2,4,6-tri-tert.butylphenol are obtained with a melting point of 130°–131.0° C. (the melting point as reported in the literature is 130°–131° C.). No impurities have been found in the product chromatographically.

What is claimed is:

1. A continuous crystallization method for purifying a tertiary alkylphenol selected from the group consisting of 4-methyl-2,6-di-tert. butylphenol, bis-(5-methyl-3-tert.butyl 2-hydroxyphenol)methane and 2,4,6-tri-tert.butylphenol from alkylated phenol impurities comprising contacting an impure tertiary alkylphenol with a solvent, inert to the alkylphenol and capable of removing said alkylated phenol impurities in a continuous action crystallizer equipped with a vertical washing element at a rate of 0.12 to 0.31 hr$^{-1}$ and temperature varying from 15° C. to 20° C. to form tertiary alkylphenol crystals; passing said tertiary alkylphenol crystals over the washing element in the form of a layer of crystals moving downward at a rate of 0.1 to 1.0 hr$^{-1}$; and washing the layer of crystals with a counter-current stream of said solvent, moving upward at a rate of 0.09 to 0.35 hr$^{-1}$.

2. A method as claimed in claim 1, wherein the solvent is selected from the group consisting of ethyl alcohol, methyl alcohol, isopropyl alcohol, acetone, and gasoline.

3. A method as claimed in claim 2, wherein as the solvent use is made of ethyl alcohol.

4. A method as claimed in claim 2, wherein as the solvent use is made of methyl alcohol.

5. A method as claimed in claim 2, wherein as the solvent use is made of gasoline.

6. A method as claimed in claim 1, wherein the ratio of the height of the moving crystal layer to its diameter is no less than 3.

7. A method as claimed in claim 1, wherein the purity of the alkylphenol product is at least 99.99 weight %.

8. A method as claimed in claim 1, wherein the solvent is recycled to the crystallizing step.

* * * * *